(12) United States Patent
Liu et al.

(10) Patent No.: US 12,011,581 B2
(45) Date of Patent: Jun. 18, 2024

(54) MICRO MAGNETIC-HYDRAULIC SUSPENSION CENTRIFUGAL BLOOD PUMP

(71) Applicant: SHANGHAI DONGXIN BIOMEDICAL TECHNOLOGY CO., LTD., Shanghai (CN)

(72) Inventors: Zhongmin Liu, Shanghai (CN); Feng Wan, Shanghai (CN); Yuanyi Peng, Shanghai (CN); Guorong Li, Shanghai (CN)

( * ) Notice: Subject to any disclaimer, the term of this patent is extended or adjusted under 35 U.S.C. 154(b) by 0 days.

(21) Appl. No.: 17/597,435

(22) PCT Filed: Mar. 1, 2021

(86) PCT No.: PCT/CN2021/078407
§ 371 (c)(1),
(2) Date: Jan. 6, 2022

(87) PCT Pub. No.: WO2022/141782
PCT Pub. Date: Jul. 7, 2022

(65) Prior Publication Data
US 2024/0024658 A1 Jan. 25, 2024

(30) Foreign Application Priority Data
Dec. 29, 2020 (CN) .......................... 202011599149.8

(51) Int. Cl.
*A61M 60/232* (2021.01)
*A61M 60/422* (2021.01)

(52) U.S. Cl.
CPC ........ *A61M 60/232* (2021.01); *A61M 60/422* (2021.01); *A61M 2205/0211* (2013.01)

(58) Field of Classification Search
CPC .............. A61M 60/232; A61M 60/422; A61M 2205/0211; F04D 29/0566
See application file for complete search history.

(56) References Cited

U.S. PATENT DOCUMENTS 5,399,074 A * 3/1995 Nose .................... A61M 60/825
417/423.12
5,713,730 A * 2/1998 Nose .................... A61M 60/422
417/424.2

(Continued)

*Primary Examiner* — Thomas Fink
(74) *Attorney, Agent, or Firm* — Zhigang Ma

(57) ABSTRACT

The present disclosure relates to a micro magnetic-hydraulic suspension centrifugal blood pump, which is a pump and motor integrated device. The blood pump includes a pump housing, a rotor, an impeller, a servo motor, an inner magnetic core group, an outer magnetic ring group, a limiting device, and a suture snap ring device; the rotor and the impeller are seamlessly connected into a whole; the rotor is arranged in an inner pipe of the blood pump; the servo motor drives the rotor to drive the impeller to do work; the inner magnetic core group is arranged at a lower end inside the rotor; the outer magnetic ring group and a wrapping sleeve are upright in a pump cavity lower shell; an inner and outer magnetic combination can achieve a radial magnetic suspension effect of the impeller; a ceramic sheet and a ceramic cone form a temporary limiting bearing; a top end of a vane of the impeller is provided with an inclined surface; and the pump can generate hydraulic suspension during working. According to the technical solution of the present disclosure, the rotor impeller can work in a steady suspended state, which overcomes the friction effect of a mechanical bearing; the structures in the pump are simple and fluent, which can greatly reduce hemolysis and thromboembolic complications; the blood pump has a small volume and light weight, so that the invasiveness of operation is low, and the safety and the practicability can be improved.

10 Claims, 3 Drawing Sheets

(56) References Cited

U.S. PATENT DOCUMENTS

| | | | | |
|---|---|---|---|---|
| 6,155,969 | A * | 12/2000 | Schima | A61M 60/113 |
| | | | | 600/16 |
| 6,158,984 | A * | 12/2000 | Cao | A61M 60/226 |
| | | | | 417/423.1 |
| 10,145,376 | B2 * | 12/2018 | Kumano | A61M 60/804 |
| 10,363,348 | B2 * | 7/2019 | Tanaka | F04D 29/043 |
| 10,660,996 | B2 * | 5/2020 | Foster | A61M 60/178 |
| 2003/0233021 | A1 * | 12/2003 | Nose | A61M 60/419 |
| | | | | 600/16 |
| 2015/0112119 | A1 | 4/2015 | Buckberry | |
| 2018/0050142 | A1 | 2/2018 | Siess et al. | |
| 2018/0228953 | A1 | 8/2018 | Siess et al. | |
| 2020/0276368 | A1 * | 9/2020 | Reyes | A61M 60/148 |

\* cited by examiner

MICRO MAGNETIC-HYDRAULIC SUSPENSION CENTRIFUGAL BLOOD PUMP

TECHNICAL FIELD

The embodiment of this specification relates to the technical field of medical devices, specifically to a micro magnetic-hydraulic suspension centrifugal blood pump.

BACKGROUND

An artificial heart uses mechanical power to replace or assist the pump work of the human failing heart, so it is also referred to as "blood pump". It provides a new treatment method for the treatment of patients with an advanced heart failure. At present, blood pumps used in the international market are mainly divided into two categories: centrifugal blood pumps and axial flow blood pumps. The two types of blood pumps can be divided into a bearing type structure and a suspension type structure according to internal structures. The blood pump of the bearing type structure is usually called a second-generation blood pump, which has the following main disadvantages: a bearing is easy to wear, which seriously restricts the service life of the blood pump. The suspension type structure is usually called a third-generation blood pump, with magnetic suspension or hydraulic suspension. Such a structure without a bearing has long service life, has no frictional heat and no local blood flow retention area, which can better prevent thrombosis, but there are new problems below. Firstly, the magnetic suspension structure is complicated, so that detection, feedback and control systems need to be added, and the volume of the blood pump will be increased, which increases the invasiveness of operation. For example, the volume and weight of the third-generation magnetic suspension blood pump HeartMate III is more than three times that of the second-generation blood pump Jarvik2000. Secondly, the internal fluid mechanical structure is complex, it is difficult to overcome dead ends of blood flow, and thrombi are easily formed in the dead ends.

It can be seen that reducing the volume and weight of the suspension type blood pump, simplifying structures inside the pump, and reducing complications such as hemolysis and thrombosis are problems that need to be solved in blood pumps.

SUMMARY

The technical problem to be solved in the embodiment of this specification is to overcome the shortcomings in the existing art, and a micro magnetic-hydraulic suspension centrifugal blood pump with small volume, light weight, and simple structure is provided.

In order to achieve the foregoing objectives, the embodiment of this specification adopt the following technical solutions:

A micro magnetic-hydraulic suspension centrifugal blood pump includes a pump housing, a rotor, an impeller, a servo motor, an inner magnetic core group, an outer magnetic ring group, a limiting device, and a suture snap ring device; the rotor is seamlessly connected with the impeller; the rotor is arranged in an inner pipe of the blood pump and is driven by the servo motor to drive the impeller to do work;

the inner magnetic core group includes a plurality of circular magnetic sheets arranged at a lower end inside the rotor; the outer magnetic ring group includes a plurality of magnetic rings arranged inside a lower end of the pump housing and surrounding the inner magnetic core group;

the limiting device includes a ceramic sheet and a ceramic cone; the ceramic sheet is inlaid in a lower end of the rotor impeller; the ceramic cone is arranged inside the lower end of the pump housing and is opposite to the ceramic sheet in the center.

Alternatively, the blood pump further includes a suture snap ring device; the suture snap ring device is arranged outside the pump housing and is used for fixing the blood pump and the cardiac apex.

Alternatively, the inner magnetic core group is composed of three circular magnetic sheets, and the outer magnetic ring group is composed of three magnetic rings; or, the inner magnetic core group is composed of four circular magnetic sheets, and the outer magnetic ring group is composed of four magnetic rings; or, the inner magnetic core group is composed of five circular magnetic sheets, and the outer magnetic ring group is composed of five magnetic rings; or, the inner magnetic core group is composed of six circular magnetic sheets, and the outer magnetic ring group is composed of sixth magnetic rings.

Alternatively, the inner magnetic core group and the outer magnetic ring group are each formed by forcibly adhering strong-magnetic neodymium iron boron materials, with the same polarities facing each other.

Alternatively, an inclined surface in the middle of a top of the impeller is a hydraulic suspension structure.

Alternatively, the impeller is sheetlike, including a plurality of vanes; and roots of the vanes are connected with the rotor.

Alternatively, the impeller includes 3-5 vanes.

Alternatively, the pump housing includes an inlet pipeline, a pump cavity cover, and a pump cavity lower shell;
the inlet pipeline includes an outer sleeve and an inner pipe;
the outer sleeve and the inner pipe are of coaxial structures, with inlet ends directly connected with each other and the other ends connected to the pump cavity cover;
a circle of sandblast titanium powder coating layer is provided on an outer surface of the outer sleeve;
the pump cavity cover is of a circular ring shape and is concentrically connected with the inner pipe, and an excircle is connected with the pump cavity lower shell;
a circular boss is provided at an inner bottom of the pump cavity lower shell, and a pump outlet is provided on a side edge.

Alternatively, the servo motor includes a rotor magnetic steel, a stator core, and a stator winding;
the rotor magnetic steel is arranged inside the rotor; the stator core and the stator winding are arranged on an inner wall of the inlet pipeline, that is, internally arranged between the inner pipe and the outer sleeve;
the rotor magnetic steel and the rotor are combined into a whole, and the stator core and the stator winding are combined with the inlet pipeline into a whole.

Alternatively, the servo motor further includes a telecommunication transmission line; one end of the telecommunication transmission line is connected with the stator winding, and the other end extends to the outside of the body and is connected with a control system.

Alternatively, the suture snap ring device includes a suture ring and a snap ring mechanism; the snap ring mechanism includes a hook ring and a base ring.

The embodiment of this specification adopting at least one of the above technical solutions can achieve the following beneficial effects:

The suspension of the embodiment of this specification is passive permanent magnet suspension, and no complex detection, feedback, and control systems are needed, so that the structure is simpler, the performance is stable, and the technical reliability and safety of use of the blood pump can be greatly improved; the volume and weight of the blood pump are small, so that the invasiveness of operation of the blood pump can be reduced, and the practicability can be improved; and the internal structure of the full-suspension blood pump is simple and fluent, which avoids dead spaces or dead ends and can also effectively prevent thrombosis.

BRIEF DESCRIPTION OF THE DRAWINGS

In order to describe the embodiments of this specification or the technical solutions in the existing technology more clearly, drawings required to be used in the embodiments or the illustration of the existing technology will be briefly introduced below. Obviously, the drawings in the illustration below are only some embodiments of the embodiments in this specification. Those ordinarily skilled in the art also can obtain other drawings according to these drawings without doing creative work.

Figure 1:
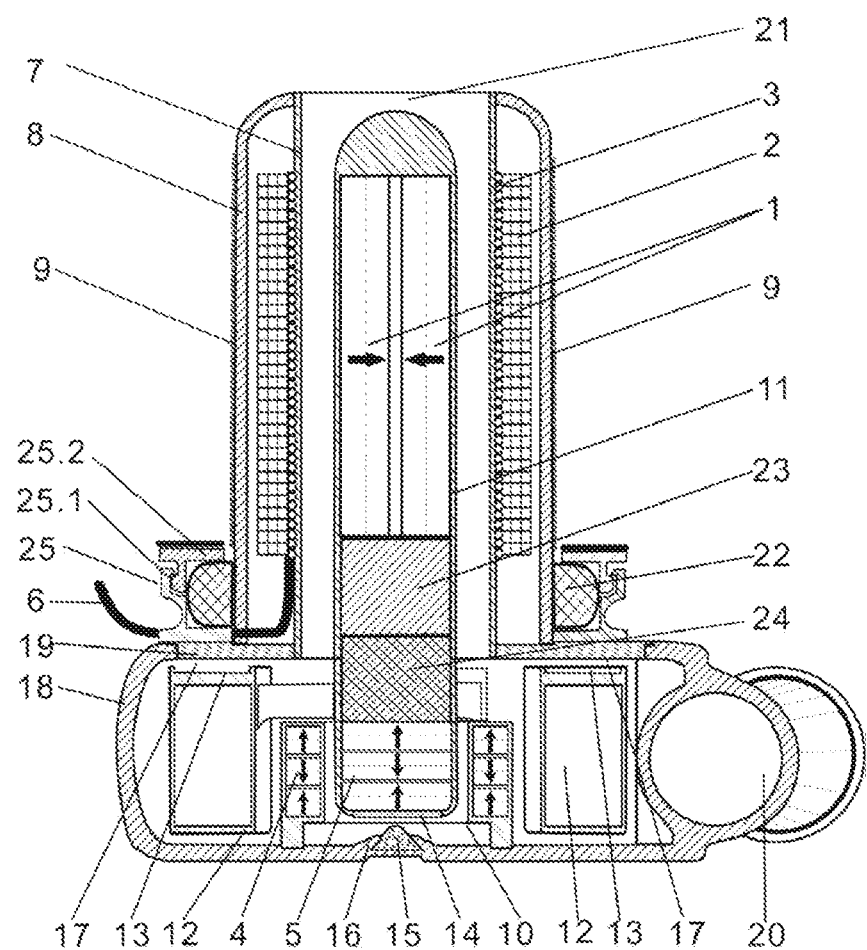
FIG. 1 is a schematic structural diagram of a section of a micro magnetic-hydraulic suspension centrifugal blood pump provided by an embodiment of this specification.

Reference signs in the drawings: rotor magnetic steel—1, stator core—2, stator winding—3, outer magnetic ring group—4, spacer—4.1, inner magnetic core group—5, telecommunication transmission line—6, inner pipe—7, outer sleeve—8, titanium powder coating layer—9, magnetic ring sleeve—10, sleeve foot—10.1, rotor—11, impeller—12, inclined surface—13, ceramic sheet—14, ceramic cone—15, circular boss—16, wedge slot—17, pump cavity lower shell—18, pump cavity cover—19, pump outlet—20, pump inlet—21, suture ring—22, soft magnetic sheet—23, gasket—24, snap ring mechanism—25, hook ring—25.1, base ring 25.2, first backward axial force—F1, second backward axial force—F2, third backward axial force—F3, and forward axial force—F4.

DETAILED DESCRIPTION OF THE EMBODIMENTS

In order to make the purposes, technical solutions, and advantages of the embodiment of this specification clearer, the technical solutions of the embodiment of this specification will be described in detail below. It is apparent that the described embodiments are a part of the embodiments of this specification, not all the embodiments. Based on the embodiments in the embodiments of this specification, all other embodiments obtained by those of ordinary skill in the art without creative work shall fall within the protection scope of the embodiments of this specification.

Specific implementations of the embodiments are further described below in combination with the drawings of the embodiments of this specification.

Figure 2:
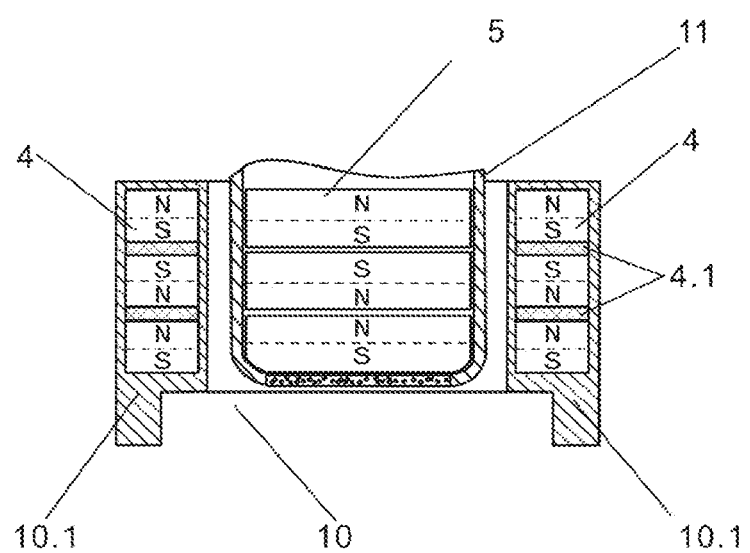
FIG. 2 is a sectional view of a combination of an outer magnetic ring group and an inner magnetic core group provided by an embodiment of this specification.
Figure 3:
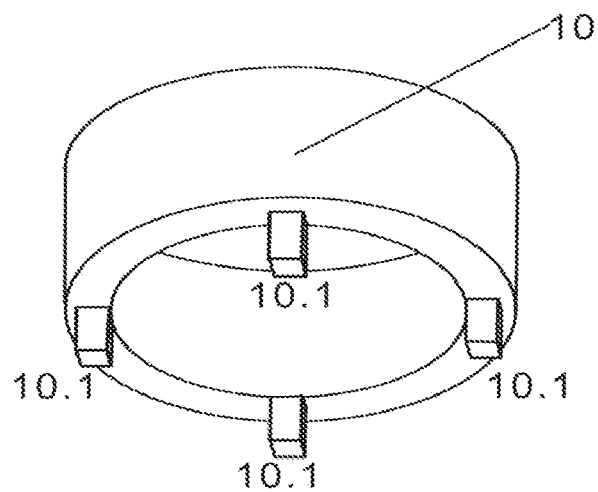
FIG. 3 is a schematic diagram of a stereo structure of a magnetic ring sleeve provided by an embodiment of this specification.
Figure 4:
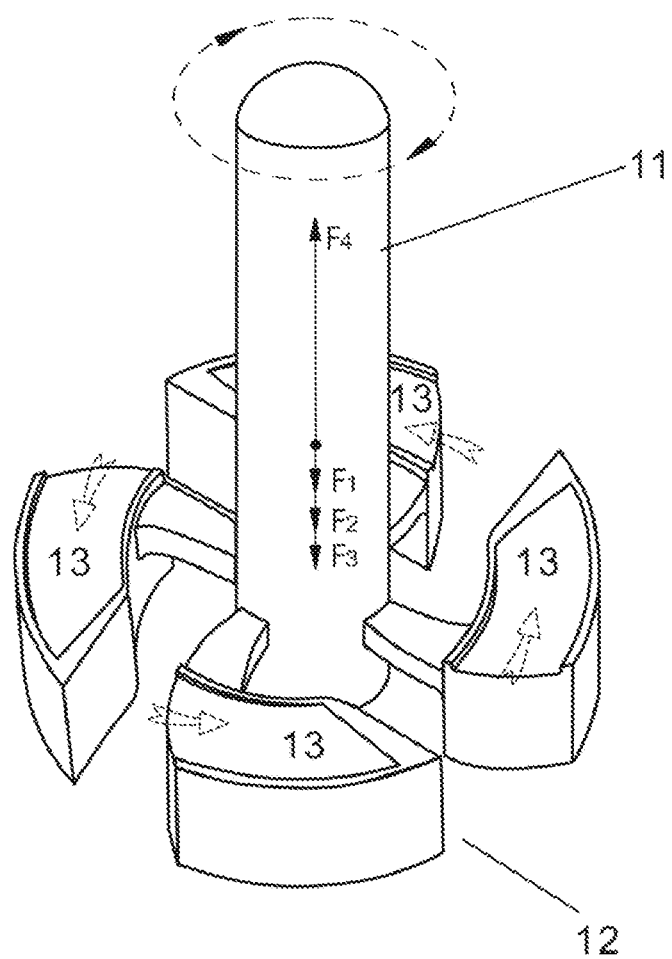
FIG. 4 is a three-dimensional schematic diagram of stress analysis of a rotor and an impeller provided by an embodiment of this specification.

Referring to FIG. 1 to FIG. 4, an embodiment of this specification provides a micro magnetic-hydraulic suspension centrifugal blood pump, including a pump device, a servo motor, a suspension limiting system, and a suture snap ring device.

The pump device includes a pump housing, a rotor 11, and an impeller 12.

The pump housing includes an inlet pipeline, a pump cavity cover 19, and a pump cavity lower shell 18.

The inlet pipeline includes an inner pipe 7 and an outer sleeve 8.

The inner pipe 7 and the outer sleeve 8 are of coaxial structures, with inlet ends directly connected with each other and the other ends connected to the pump cavity cover 19. Joints are all seamlessly welded to prevent leakage.

An excircle of the outer sleeve 8 is coarsened, which is provided with a circle of sandblast titanium powder coating layer 9, which can promote formation of a layer of closed-loop inner film at a cardiac apex socket.

There is a cavity between the outer sleeve 8 and the stator core 2, which can achieve heat resistance and cooling effects to improve the safety of the blood pump and the motor.

The pump cavity cover 19 is of a circular ring shape; an opening in the center of the pump cavity cover is concentrically connected with the inner pipe 7; an excircle is connected with the pump cavity lower shell 18; and a joint needs to be welded to prevent leakage.

A circular boss 16 is provided at an inner bottom of the pump cavity lower shell 18, and a pump outlet 20 is provided on a side edge. After internal parts have been mounted, the pump cavity cover 19 and the pump cavity lower shell 18 are buckled and subjected to sealing welding.

The rotor 11 and the impeller 12 are seamlessly connected into a whole.

The rotor 11 is driven by the servo motor to drive the impeller 12 to do work, which promotes blood to constantly flows in from the pump inlet 21; and after being centrifuged, the blood flows out from the pump outlet 20.

The impeller 12 is composed of four hollow vanes. The vanes are uniformly distributed at a root part of the rotor 11 and are seamlessly connected with the rotor into a whole.

The servo motor mainly includes a rotor magnetic steel 1, a stator core 2, a stator winding 3, and a telecommunication transmission line 6.

The rotor magnetic steel 1 is arranged in the rotor 11. The stator core 2 and the stator winding 3 are sleeved on an outer wall of the inner pipe 7. The rotor magnetic steel 1 is radially arranged in the center of the sleeve of the stator core 2 and the stator winding 3; and the rotor magnetic steel 1 shifts forwards at an axial position.

The telecommunication transmission line 6 is used for transmitting electric energy and electric signals. One end of the telecommunication transmission line is connected with the stator winding 3, and the other end extends to the outside of the body and is connected with a control system.

Since the servo motor and the pump device are combined into a whole, "pump-motor integration" is realized.

The suspension limiting system includes a magnetic suspension combination, a hydraulic suspension structure, and a limiting device.

The magnetic suspension combination includes an inner magnetic core group 5 and an outer magnetic ring group 4 which cooperate with each other to cause the rotor and the impeller to realize radial magnetic suspension.

The inner magnetic core group 5 is formed by coaxially stacking three circular magnetic sheets arranged at a lower end inside the rotor. The outer magnetic ring group 4 is formed by coaxially stacking three magnetic rings. The magnetic rings do not directly contact, between which extremely thin spacers 4.1 with the same sizes are adhered. The magnetic ring group 4 is wrapped inside a magnetic ring sleeve 10. The magnetic ring sleeve 10 has several sleeve feet 10.1. The sleeve feet 10.1 are embedded into the pump cavity lower shell 18.

The circular magnetic sheets or magnetic rings of the inner magnetic core group 5 and the outer magnetic ring group 4 have an axial magnetic direction and are forcibly adhered together, with the same polarities facing each other.

Alternatively, the inner magnetic core group 5 may be formed by combining four circular magnetic sheets, and the outer magnetic ring group 4 is formed by combining four magnetic rings; or the inner magnetic core group 5 may be formed by combining five circular magnetic sheets, and the outer magnetic ring group 4 is formed by combining five magnetic rings; or the inner magnetic core group 5 may be formed by combining six circular magnetic sheets, and the outer magnetic ring group 4 is formed by combining six magnetic rings. The inner magnetic core group 5 and the outer magnetic ring group 4 are basically centered and aligned during mounting.

Preferably, magnetic materials of the inner magnetic core group 5 and the outer magnetic ring group 4 are strong magnetic neodymium iron boron.

A soft magnetic sheet 23 and a gasket 24 are arranged between the rotor magnetic steel 1 and the inner magnetic core group 5, which can achieve magnetic shielding and anti-interference effects and can enhance the magnetic suspension effect and improve the working efficiency of the blood pump. In particular, the soft magnetic sheet 23 is a magnetoconductive material such as silicon steel and iron, and the gasket 24 is a non-magnetoconductive material.

The limiting device includes a ceramic sheet 14 and a ceramic cone 15. The ceramic sheet 14 is inlaid at a lower end of the rotor impeller 12, and the ceramic cone 15 is inlaid in the circular boss 16 of the pump cavity lower shell and is centered and directly opposite to the ceramic sheet 14. When the blood pump is stationary or in a low-speed state, under the pressure action of the rotor impeller, the ceramic cone 15 presses against the ceramic sheet 14, which can play a role of a group of temporary sliding bearings to well limit the impeller and support the turning on of the blood pump.

The hydraulic suspension structure is that the middle part of a top of the impeller 12 is inclined. That is, the middle part of the top of the vane is inclined from an incident flow edge to a lee side of an inlet. The inclined surface 13 and an inner surface of the pump cavity cover 19 form a wedge space. Furthermore, two sides of the slope have edges flush with a top surface, which can prevent a liquid flow from overflowing. When the blood pump works, under the action of a centrifugal force, there is liquid flow entering a wedge slot 17, which generates a hydraulic pressure due to extrusion. An axial force pushes away the impeller 12, so that the impeller cannot contact the pump cavity cover 19 all the time.

Alternatively, an inclination angle of the inclined surface 13 is 1-10 degrees.

The suture snap ring device is at a root part of the outer sleeve 8 close to the pump cavity cover 19, and includes a suture ring 22 and a snap ring mechanism 25, so as to be used for connecting the cardiac apex with the blood pump and fixing the blood pump. During an operation, a base ring 25.2 is sutured on the cardiac apex; after perforation, a pump inlet is inserted into the ventricle from a hole; and when a hook ring 25.1 is hooked on the base ring 25.2, the blood pump is fixed.

After the micro magnetic-hydraulic suspension centrifugal blood pump provided by the embodiment of this specification is steadily started, it is necessary to analyze how the rotor impeller realizes suspended running. Suspension can be divided into radial suspension and axial suspension.

The radial suspension is mainly realized by the magnetic suspension combination. The inner magnetic core group 5 and the outer magnetic ring group 4 are radially repulsive of each other due to magnetic forces. The repulsive force is high enough to overcome and balance various radial forces, so that the rotor impeller is always limited at the centers of the inner pipe 7 and the pump cavity. By the fixed-axis effect of a gyroscope, a good radial magnetic suspension effect can be achieved.

The axial suspension is hydraulic suspension. It is necessary to analyze an axial force to know how the axial suspension is achieved. The blood pump will be affected by a plurality of axial forces during high-speed work. The axial forces can be divided into a weak axial force and a strong axial force. The weak axial force mainly includes an axial component of the gravity of the rotor impeller and axial forces of other factors and these are weak influence factors. The strong axial force mainly includes four axial forces which can be analyzed by illustration of FIG. 4. F4 is a forward axial force (pointing to the pump inlet), and F1, F2, and F3 are three backward axial forces (facing away from the pump inlet). F1 is generated because the motor core always has an automatic binding force on the motor magnetic steel to cause it to be axially centered. When the magnetic steel axially moves forwards relative to the core, it is pulled by a backward tension. When the magnetic steel axially moves backwards relative to the core, it is pulled by a forward tension. In this description example, since the rotor magnetic steel 1 moves forwards, F1 is a relatively low axially backward force, which has nothing to do with the rotating speed of the pump. F2 is an axial component of an impact force generated by the momentum of liquid on the impeller. The size of this force is in positive correlation with the rotating speed. F3 is an axial component of a pressure applied by the hydraulic pressure to the inclined surface 13 of the impeller 12. The size of this force is in positive correlation with the rotating speed by geometrical progression, but is in negative correlation with the size of the wedge space. F4 is generated by a pressure difference between a low hydraulic pressure on the inner surface as well as suction inlet of the pump cavity cover 19 and a lower cover surface during work of the pump. This force rapidly increases as the rotating speed of the pump increases after the pump is started. When the rotating speed reaches a certain value, and F4 is greater than a sum of F1, F2, and F3, F4 drives the rotor impeller and the ceramic sheet 14 to be separated from the ceramic cone 15 and axially move forwards. As a wheel gets close to the pump cavity cover 19, the wedge space becomes small, and the generated axial component F3 of the hydraulic pressure increases in geometrical progression. F3 will automatically resist F4. When a resultant force balance of the axial components is achieved, the rotor impeller is forced to stop axially moving, and F3 will no longer increase. That is, within a certain rotating speed range, the axial forces on the rotor impeller can be automatically balanced, and the axial suspension is automatically achieved.

As mentioned above, combining the radial suspension with the axial suspension of the rotor impeller can realize steady suspended running.

The embodiment of this specification can achieve the following technical effects:

Compared with an existing mechanical bearing blood pump, the blood pump of the embodiment of this specification has the advantages that in the suspended state during normal work, no friction occurs to a bearing, hemolysis can be reduced, the life of the blood pump can be prolonged, and thromboembolic complications caused by frictional heat can also be reduced.

Compared with the existing magnetic suspension blood pump, the blood pump of this specification has the advantages that the suspension of the embodiment of this specification is passive permanent magnet suspension, and no complex detection, feedback, and control systems are needed, so that the structure is simpler, the performance is stable, and the technical reliability and safety of use of the blood pump can be greatly improved; the volume and weight of the blood pump are small, so that the invasiveness of operation of the blood pump can be reduced, and the practicability can be improved; and the internal structure of the full-suspension blood pump is simple and fluent, which avoids dead spaces or dead ends and can also effectively prevent thrombosis.

In the description of the present specification, descriptions of the reference terms such as "one embodiment", "some embodiments", "examples", "specific examples," or "some examples" mean that specific features, structures, materials or characteristics described in combination with the embodiments or examples are included in at least one embodiment or example of the present invention. In this specification, indicative expressions of the above terms do not necessarily refer to the same embodiments or examples. Moreover, the described specific features, structures, materials or characteristics can be combined in any one or more embodiments or examples in a suitable manner. Although the embodiments of the present disclosure have been shown and described above, it can be understood that the above embodiments are exemplary and should not be construed as limiting the present disclosure. Those of ordinary skill in the art can make changes, modifications, substitutions, and variations to the above-mentioned embodiments within the scope of the present disclosure.

What is claimed is:

1. A micro magnetic-hydraulic suspension centrifugal blood pump, comprising a pump housing, a rotor, an impeller, a servo motor, an inner magnetic core group, an outer magnetic ring group, a limiting device, and a suture snap ring device, wherein the rotor is seamlessly connected with the impeller; the rotor is arranged in an inner pipe of the blood pump and is driven by the servo motor to drive the impeller to do work; the inner magnetic core group comprises a plurality of circular magnetic sheets arranged at a lower end inside the rotor; the outer magnetic ring group comprises a plurality of magnetic rings arranged inside a lower end of the pump housing and surrounding the inner magnetic core group; the limiting device comprises a ceramic sheet and a ceramic cone; the ceramic sheet is inlaid in a lower end of the rotor impeller; the ceramic cone is arranged inside the lower end of the pump housing and is opposite to the center of the ceramic sheet.

2. The blood pump according to claim 1, wherein the suture snap ring device is arranged outside the pump housing and is used for fixing the blood pump and the cardiac apex.

3. The blood pump according to claim 1, wherein the inner magnetic core group is composed of three circular magnetic sheets, and the outer magnetic ring group is composed of three magnetic rings; or
the inner magnetic core group is composed of four circular magnetic sheets, and the outer magnetic ring group is composed of four magnetic rings; or,
the inner magnetic core group is composed of five circular magnetic sheets, and the outer magnetic ring group is composed of five magnetic rings; or,
the inner magnetic core group is composed of six circular magnetic sheets, and the outer magnetic ring group is composed of sixth magnetic rings.

4. The blood pump according to claim 1, wherein the inner magnetic core group and the outer magnetic ring group are each formed by forcibly adhering strong-magnetic neodymium iron boron materials, with the same polarities facing each other.

5. The blood pump according to claim 1, wherein an inclined surface in the middle of a top of the impeller is a hydraulic suspension structure.

6. The blood pump according to claim 1, wherein the impeller comprises a plurality of vanes; and roots of the vanes are connected with the rotor.

7. The blood pump according to claim 6, wherein the impeller comprises 3-5 vanes.

8. The blood pump according to claim 1, wherein the pump housing comprises an inlet pipeline, a pump cavity cover, and a pump cavity lower shell; the inlet pipeline comprises an outer sleeve and an inner pipe; the outer sleeve and the inner pipe are of coaxial structures, with inlet ends directly connected with each other and the other ends connected to the pump cavity cover; a circle of a sandblasted titanium powder coating layer is provided on an outer surface of the outer sleeve; the pump cavity cover is of a circular ring shape and is concentrically connected with the inner pipe, and an excircle is connected with the pump cavity lower shell; a circular boss is provided at an inner bottom of the pump cavity lower shell, and a pump outlet is provided on a side edge of the lower shell.

9. The blood pump according to claim 8, wherein the servo motor comprises a rotor magnetic steel, a stator core, and a stator winding;
the rotor magnetic steel is arranged inside the rotor; the stator core and the stator winding are arranged on an inner wall of the inlet pipeline, that is, internally arranged between the inner pipe and the outer sleeve;
the rotor magnetic steel and the rotor are combined into a whole, and the stator core and the stator winding are combined with the inlet pipeline into a whole.

10. The blood pump according to claim 9, wherein the servo motor further comprises a telecommunication transmission line; one end of the telecommunication transmission line is connected with the stator winding, and the other end extends to the outside of the pump housing and is connected with a control system.

* * * * *